United States Patent
Sabesan et al.

(10) Patent No.: US 12,070,611 B2
(45) Date of Patent: Aug. 27, 2024

(54) STIMULATION SYSTEM WITH MONOLITHIC-LEAD COMPONENT CONNECTED TO SKULL MOUNT PACKAGE

(71) Applicant: Verily Life Sciences LLC, South San Francisco, CA (US)

(72) Inventors: Shivkumar Sabesan, Campbell, CA (US); Bo Lu, South San Francisco, CA (US); Annapurna Karicherla, South San Francisco, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 329 days.

(21) Appl. No.: 17/276,439

(22) PCT Filed: Sep. 13, 2019

(86) PCT No.: PCT/US2019/051168
§ 371 (c)(1),
(2) Date: Dec. 16, 2021

(87) PCT Pub. No.: WO2020/060882
PCT Pub. Date: Mar. 26, 2020

(65) Prior Publication Data
US 2022/0126106 A1    Apr. 28, 2022

Related U.S. Application Data

(60) Provisional application No. 62/732,671, filed on Sep. 18, 2018.

(51) Int. Cl.
*A61N 1/375* (2006.01)
*A61N 1/05* (2006.01)
*A61N 1/36* (2006.01)

(52) U.S. Cl.
CPC ....... *A61N 1/37514* (2017.08); *A61N 1/0534* (2013.01); *A61N 1/0539* (2013.01); *A61N 1/36125* (2013.01)

(58) Field of Classification Search
CPC ............. A61N 1/37514; A61N 1/0534; A61N 1/0539; A61N 1/36125; A61N 1/36082;
(Continued)

(56) References Cited

U.S. PATENT DOCUMENTS 5,324,322 A   6/1994  Grill, Jr. et al.
6,210,339 B1  4/2001  Kiepen et al.
(Continued)

FOREIGN PATENT DOCUMENTS

WO   2010055453 A1    5/2010
WO   WO-2016201151 A1 * 12/2016 ............... A61B 5/24

OTHER PUBLICATIONS

U.S. Appl. No. 16/658,596, Notice of Allowance, Mailed On Mar. 25, 2022, 8 pages.
(Continued)

*Primary Examiner* — Ankit D Tejani
*Assistant Examiner* — Joshua Brendon Solomon
(74) *Attorney, Agent, or Firm* — Kilpatrick Townsend & Stockton LLP

(57) ABSTRACT

A stimulation system can include one or more stimulating components, each of which can include one or more electrodes and one or more leads. Each lead can be connected at a first end of the lead to an electrode of the one or more electrodes and can be connected at a second end of the lead to a bonding pad of the one or more bonding pads. The stimulation system can also include a cylindrical substrate. Each stimulating component can be secured to a surface of the cylindrical substrate. The stimulation system can further include a skull-mount package that includes electronics that (Continued)

identify stimulation parameters. The bonding pads can be electrically connected to the electronics. The skull-mount package can further include one or more bonding pads. Each lead can be directly electrically and physically connected to a bonding pad of the one or more bonding pads.

18 Claims, 10 Drawing Sheets

(58) Field of Classification Search
CPC .......... A61N 1/375; A61B 5/24; A61B 5/291; A61B 5/6868
See application file for complete search history.

(56) References Cited

U.S. PATENT DOCUMENTS

| | | | |
|---|---|---|---|
| 6,662,035 B2 | 12/2003 | Sochor | |
| 8,380,325 B2 | 2/2013 | McDonald | |
| 9,829,028 B2 | 11/2017 | Changsrivong et al. | |
| 11,395,923 B2 | 7/2022 | Lu et al. | |
| 2003/0135253 A1 | 7/2003 | Kokones et al. | |
| 2005/0137665 A1 | 6/2005 | Cole | |
| 2007/0261115 A1* | 11/2007 | Gerber | A61N 1/0534 726/22 |
| 2008/0096310 A1 | 4/2008 | Modi et al. | |
| 2008/0147158 A1* | 6/2008 | Zweber | A61N 1/0534 607/122 |
| 2010/0065963 A1 | 3/2010 | Eldridge et al. | |
| 2011/0301665 A1* | 12/2011 | Mercanzini | A61B 5/6868 607/45 |
| 2012/0071870 A1 | 3/2012 | Salahieh et al. | |
| 2013/0282090 A1 | 10/2013 | Decre et al. | |
| 2014/0324117 A1 | 10/2014 | Bedenbaugh | |
| 2015/0157862 A1 | 6/2015 | Greenberg et al. | |
| 2015/0165191 A1* | 6/2015 | Frericks | A61N 1/0551 607/137 |
| 2015/0273181 A1* | 10/2015 | Leeflang | A61M 25/005 606/41 |
| 2016/0128588 A1* | 5/2016 | Melosh | A61B 5/24 607/116 |
| 2016/0144078 A1 | 5/2016 | Young et al. | |
| 2016/0144165 A1 | 5/2016 | Young et al. | |
| 2016/0144166 A1* | 5/2016 | Decré | A61B 5/24 607/116 |
| 2016/0144168 A1 | 5/2016 | Tol et al. | |
| 2016/0144185 A1* | 5/2016 | Tol | A61M 5/1723 604/93.01 |
| 2016/0351292 A1 | 12/2016 | Toth et al. | |
| 2017/0065813 A1 | 3/2017 | Chen | |
| 2017/0319846 A1 | 11/2017 | Plachta et al. | |
| 2018/0117312 A1 | 5/2018 | Schmidt et al. | |
| 2018/0169406 A1 | 6/2018 | Shah et al. | |
| 2018/0229041 A1 | 8/2018 | Pepin et al. | |
| 2018/0345009 A1* | 12/2018 | Shah | A61N 1/0551 |

OTHER PUBLICATIONS

"Bal Contact® Electrical Contacts", Bal Seal Engineering, Available Online at https://www.balseal.com/contact/, Oct. 16, 2019, pp. 1-2.
Application No. PCT/US2019/051165, International Search Report and Written Opinion, Mailed On Feb. 4, 2020, 14 pages.
PCT/US2019/051165, "Invitation to Pay Additional Fees and, Where Applicable, Protest Fee", Dec. 10, 2019, 10 pages.
Application No. PCT/US2019/051168, International Search Report and Written Opinion, Mailed On Dec. 18, 2019, 17 pages.
Application No. PCT/US2019/057178, International Search Report and Written Opinion, Mailed On Jan. 23, 2020, 9 pages.
Application No. EP19883619.9, Extended European Search Report, Mailed On Jul. 6, 2022, 8 pages.
U.S. Appl. No. 17/277,000, Non-Final Office Action, Mailed On Jul. 20, 2023, 7 pages.
Application No. EP19778771.6, Office Action, Mailed On Jul. 10, 2023, 6 pages.
Europe Patent Application No. 19778771.6, Communication pursuant to Article 94(3) EPC, dated Feb. 27, 2023.
U.S. Appl. No. 17/277,000, Final Office Action, Mailed on Oct. 13, 2023, 9 pages.
U.S. Appl. No. 17/277,000, Notice of Allowance, Mailed on Jan. 3, 2024, 7 pages.

* cited by examiner

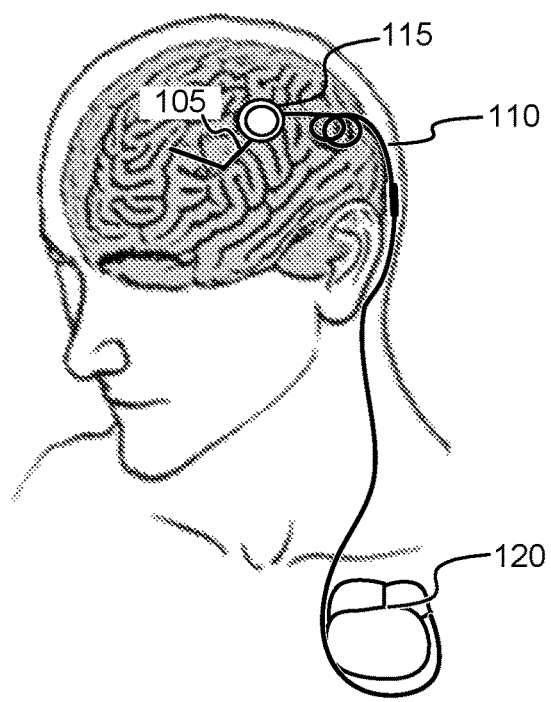
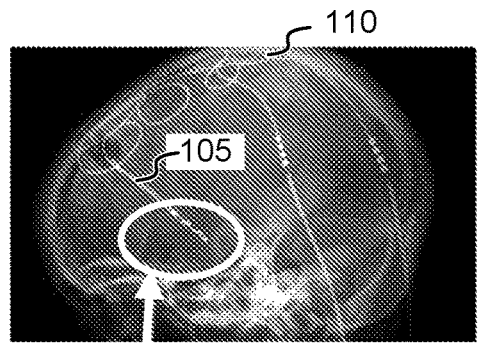
FIG. 1A
FIG. 1B
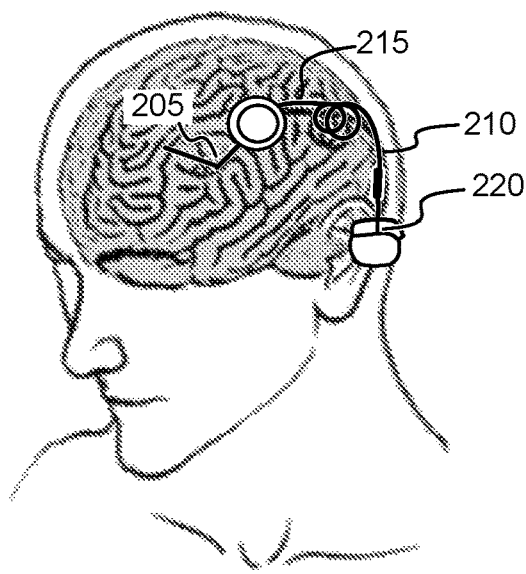
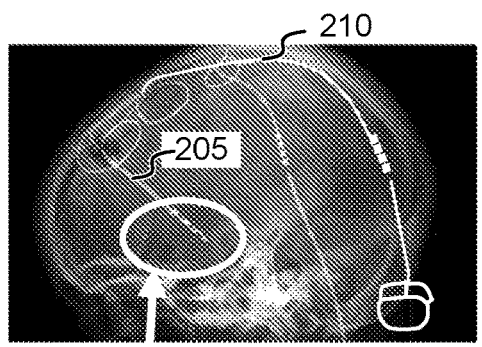
FIG. 2A
FIG. 2B

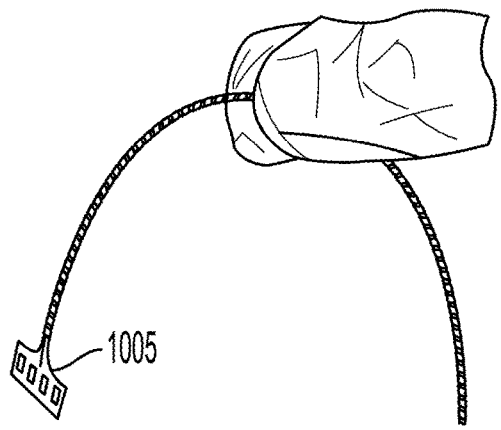
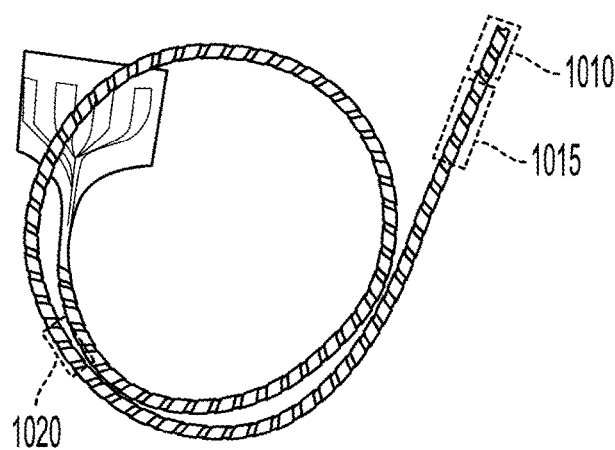
FIG. 10A
FIG. 10B
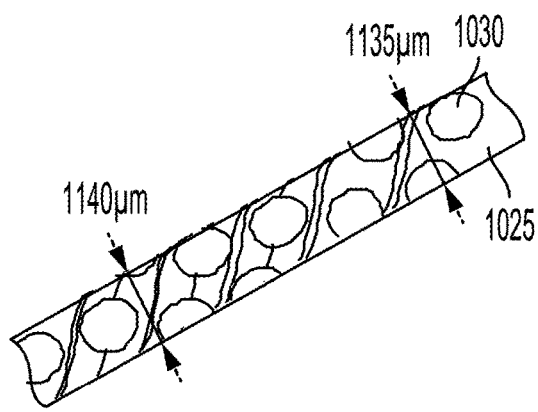
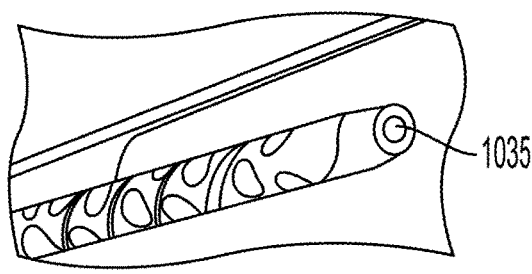
FIG. 10C
FIG. 10D
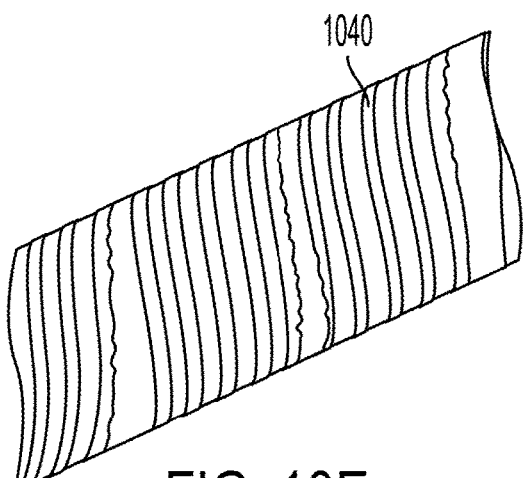
FIG. 10E

STIMULATION SYSTEM WITH MONOLITHIC-LEAD COMPONENT CONNECTED TO SKULL MOUNT PACKAGE

PRIORITY CLAIM

This application claims priority to U.S. Provisional Application No. 62/732,671 filed on Sep. 18, 2018, the entirety of which is incorporated herein by reference.

FIELD OF THE INVENTION

Embodiments relate to an implantable stimulating device. Specifically, systems include an implantable lead assembly that monolithically extends to a lead component, which connects to one or more bonding pads of a skull mount package that include stimulation circuitry.

BACKGROUND

Medical implant devices are becoming more frequently used. Some medical implant devices include a lead that delivers stimulation. For example, deep brain stimulation involves implanting a lead assembly within a particular part of the brain. The lead assembly can include a coated wire to which one or more electrodes are attached. A lead assembly can include a conductive material and can take the form of an insulated wire. A connector can connect a an end of the lead assembly to a flexible extension, which can connect (via another connector) to a neurostimulator. The neurostimulator can include circuitry that determines characteristics of stimulation to be delivered by the electrode(s).

Frequently, the neurostimulator is implanted near the collarbone. The neurostimulator can receive wireless signals from a non-implanted controller device. For example, a wireless signal can correspond to an instruction to transition to a power-on or power-off state and/or to an instruction to use a particular stimulation setting.

Thus, frequently, deep-brain-stimulation devices include multiple connectors and a sizable extension. Each connector can electrically couple the connecting components and can include (for example) a screw, a spring-lock mechanism, a welded interface or a bonded interface. However, each connection has the potential to disconnect or fracture, which can cause the device to fail. Further, the extension can cause undesired biological responses, such as subcutaneous bleeding. Thus, it would be desirable to develop a neuromodulation device that maintained connections between stimulating electrodes and circuitry but that decreased the risk of adverse events and device failure.

SUMMARY

In some embodiments, a stimulation system is provided. The stimulation system can include one or more stimulating components. Each of the one or more stimulating components can include one or more electrodes and one or more leads. Each lead of the one or more leads can be connected at a first end of the lead to an electrode of the one or more electrodes and can be connected at a second end of the lead to a bonding pad of the one or more bonding pads. The stimulation system can also include a cylindrical substrate. Each of the one or more stimulating components can be secured to a surface of the cylindrical substrate. The stimulation system can further include a skull-mount package that includes electronics that identify stimulation parameters. The one or more bonding pads can be electrically connected to the electronics. The skull-mount package can further include one or more bonding pads. Each lead of the one or more leads can be directly electrically and physically connected to a bonding pad of the one or more bonding pads.

In some embodiments, a method of manufacturing a lead assembly is provided. A set of electrodes and a set of electrical traces is disposed on a substrate. Each of the set of electrodes can be connected to an electrical trace of the set of electrical traces. A mandrel can be inserted through a tubing. The substrate can be wrapped around the tubing such that the substrate is in a helical shape. The substrate-wrapped tubing and mandrel can be inserted into a heat-shrink tube. Subsequent to the insertion, the heat-shrink tube can be heated. The heat-shrink tube can be removed from the substrate-wrapped tubing. The mandrel can be removed from the substrate-wrapped tubing.

In some embodiments, a method of implanting an implantable device is provided. A lead assembly can be inserted into a brain of a person. The lead assembly can includes one or more electrodes and one or more leads. Each lead of the one or more leads can be connected at a first end of the lead to an electrode of the one or more electrodes and can be connected at a second end of the lead to a bonding pad of the one or more bonding pads. A neurostimulator can be mounted to a skull of the person. The lead assembly can be bonded with the neurostimulator.

BRIEF DESCRIPTION OF THE DRAWINGS

Illustrative embodiments of the present invention are described in detail below with reference to the following drawing figures:

FIGS. 1A-1B show multiple views of a deep brain stimulation system that includes a neurostimulator implanted near the collar bone accordinulag to an embodiment of the invention.

FIGS. 2A-2B show multiple views of a deep brain stimulation system that includes a neurostimulator implanted beneath the scalp according to an embodiment of the invention.

FIGS. 10A-10E show various views of a lead assembly according to an embodiment of the invention.

DESCRIPTION

Figure 3:
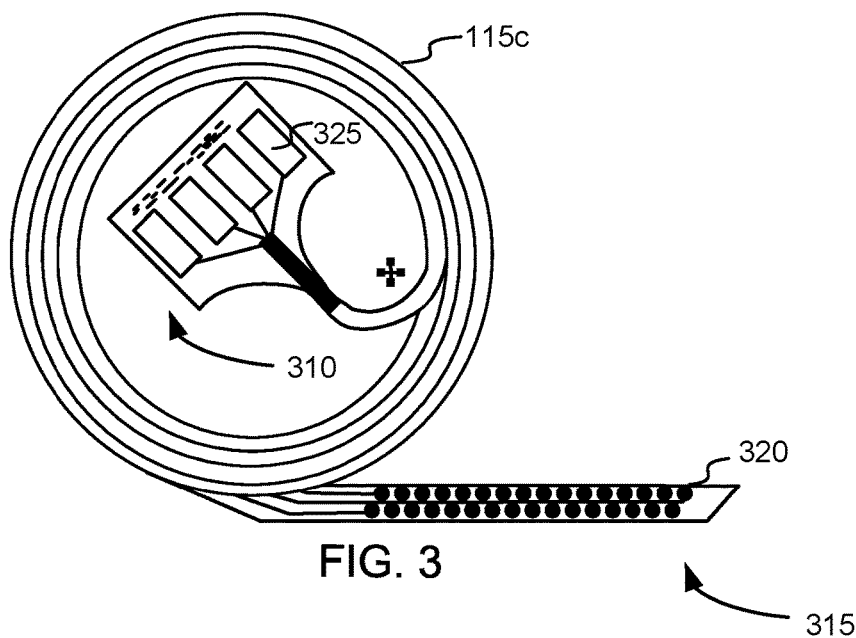
FIG. 3 shows a spiraled lead assembly according to an embodiment of the invention.

In some embodiments, a deep brain stimulation system is provided that includes a set of electrodes, a set of traces and a neurostimulator. In some instances, the deep brain stimulation system includes a monolithic thin-film lead assembly (e.g., a cable) that is fabricated using a same layer of base material (e.g., an insulating material or dielectric material, such as a polymer material). The base material and/or the monolithic thin-film lead assembly itself can have a thickness that is (for example) less than about 100 µm. The monolithic thin-film lead assembly can include a set of electrodes disposed on a first portion of the base material and a set of conductive traces that extend across a second portion of the base material. Each trace may connect to one of the set of electrodes. The monolithic nature of the thin-film lead assembly can promote stable physical and electrical connections between components of the deep brain stimulation system, as further detailed in U.S. application Number, filed on Sep. 18, 2018, which is hereby incorporated by reference in its entirety for all purposes.

The monolithic thin-film lead assembly can include one or more helically shaped components. For example, a helical portion can extend across part or all of the monolithic thin-film lead assembly at a pitch from 200 µm to 1600 µm. The pitch may, but need not, be consistent across a length of the thin-film lead assembly. The helical portion can include, is composed of and/or can support the set of electrodes and/or the set of traces. In some instances, the set of electrodes and/or the set of traces are disposed to collectively be in a helical shape. The base material and can be a supporting structure that is shaped in a hollow or solid cylindrical shape. The supporting structure may be formed with a dielectric material such as a polymer having suitable dielectric, flexibility and biocompatibility characteristics. Polyurethane, polycarbonate, silicone, polyethylene, fluoropolymer and/or other medical polymers, copolymers and combinations or blends may be used. The conductive material for the traces may be any suitable conductor such as stainless steel, silver, copper or other conductive materials, which may have separate coatings or sheathing for anticorrosive, insulative and/or protective reasons.

The helical shape can wrap around a cylindrically shaped base material. Each trace can extend between and/or electrically connect an electrode and the neurostimulator. In some instances, an end of the trace is electrically and/or physically connected to a bonding pad that is part of or is connected to the neurostimulator.

In some instances, the neurostimulator is configured to be implanted under the scalp, rather than near the collar bone. For example, the neurostimulator can be positioned between the skull and scalp in a sub-scalp or subgaleal space. This positioning can reduce an overall size of the deep brain stimulation system, as the device need not extend beyond the scalp. Further, the extension can then be shortened, which can reduce the likelihood that subcutaneous bleeding will occur. It can further yet reduce the number of incisions that are made during an implantation procedure, such that infection risk and the risk of other incision-related complications is also reduced.

FIGS. 1A-1B show multiple views of a deep brain stimulation system that includes a neurostimulator implanted near the collar bone according to an embodiment of the invention. The deep brain stimulation system can include a lead assembly 105 that includes electrodes and is implanted into the brain, such that the portion of lead assembly 105 that includes the electrodes are positioned at a target site. Lead assembly 105 can further include a flexible extension 110 that extends from the electrode portion. At least part of extension 110 can run beneath the skin and connect to a neurostimulator 120 that is implanted near the collar bone.

FIGS. 2A-2B show multiple views of a deep brain stimulation system that includes a neurostimulator implanted under the scalp according to an embodiment of the invention. The deep brain stimulation system can include a lead assembly 205 that includes electrodes and is implanted into the brain, such that the portion of lead assembly 205 that includes the electrodes are positioned at a target site. Lead assembly 205 can include an extension 210 portion. At least part of extension 210 can run beneath the skin and connect to a neurostimulator 220. Lead assembly 205 can be configured such the electrode portion and extension 210 portion are monolithic.

In this instance, neurostimulator 220 is implanted under the scalp. For example, neurostimulator 220 can be attached to a superficial surface of the skull using an adhesive, orthopedic fixation device, screw, and so on. In some instances, an entire surface of neurostimulator 220 (e.g., an entire bottom surface) can be attached to the skull (e.g., by applying an adhesive to the entire surface). In some instances, an attachment is made at one or more contact points of neurostimulator 220. For example, neurostimulator 220 can be configured to include one or more holes through which one or more screws or pins can be inserted.

In some instances, multiple lead assemblies 205 are implanted (e.g., in each cerebral hemisphere). Each of multiple lead assemblies 205 can be connected to a single neurostimulator 220.

Neurostimulator 220 can include (for example) a housing, a power source, an antenna and an electronics module (e.g., a computing system). The housing may be comprised of materials that are biocompatible such as bioceramics or bioglasses for radio frequency transparency, or metals such as titanium. The power source may be within the housing and connected (e.g., electrically connected) to the electronics module to power and operate the components of the electronics module. The antenna may be connected (e.g., electrically connected) to the electronics module for wireless communication with external devices via, for example, radiofrequency (RF) telemetry.

Neuerostimulator 220 can include one or more bonding pads that are electrically connected to the electronics module. Lead assembly 210 can be attached to the one or more bonding pads (e.g., via a welding process) to electrically connect the electronics module to electrodes in lead assembly 210. The electronics module can then apply a signal or electrical current to conductive traces of lead assembly 210 connected. The electronics module may include discrete and/or integrated electronic circuit components that implement analog and/or digital circuits capable of producing the functions attributed to the neuromodulation devices or systems such as applying or delivering neural stimulation to a patient. In various embodiments, the electronics module may include software and/or electronic circuit components such as a pulse generator that generates a signal to deliver a voltage, current, optical, or ultrasonic stimulation to a neural structure via electrodes, a controller that determines or senses electrical activity and physiological responses via the electrodes and sensors, controls stimulation parameters of the pulse generator (e.g., control stimulation parameters based on feedback from the physiological responses), and/or causes delivery of the stimulation via the pulse generator and electrodes, and a memory with program instructions operable on by the pulse generator and the controller to perform one or more processes for applying or delivering neural stimulation.

In various embodiments, the lead assembly 210 is a monolithic structure that includes a cable or lead body. In some embodiments, the lead assembly 110 further includes one or more electrode assemblies having one or more electrodes, and optionally one or more sensors. In some embodiments, the lead assembly 210 further includes a conductive connector (e.g., comprising copper, silver or gold). In certain embodiments, the connector is bonding material that bonds conductor material of the cable to the electronics module of the implantable neurostimulator 220 (e.g., at a bonding pad). A bonding material may be a conductive epoxy or a metallic solder or weld such as platinum. In other embodiments, the connector is conductive wire or conductive traces (in addition to or instead of bonding pads). In alternative embodiments, the neurostimulator 220 and the cable are designed to connect with one another via a mechanical connector, such as a pin and sleeve connector, snap and lock connector, flexible printed circuit connectors, or other means known to those of ordinary skill in the art.

Figure 4:
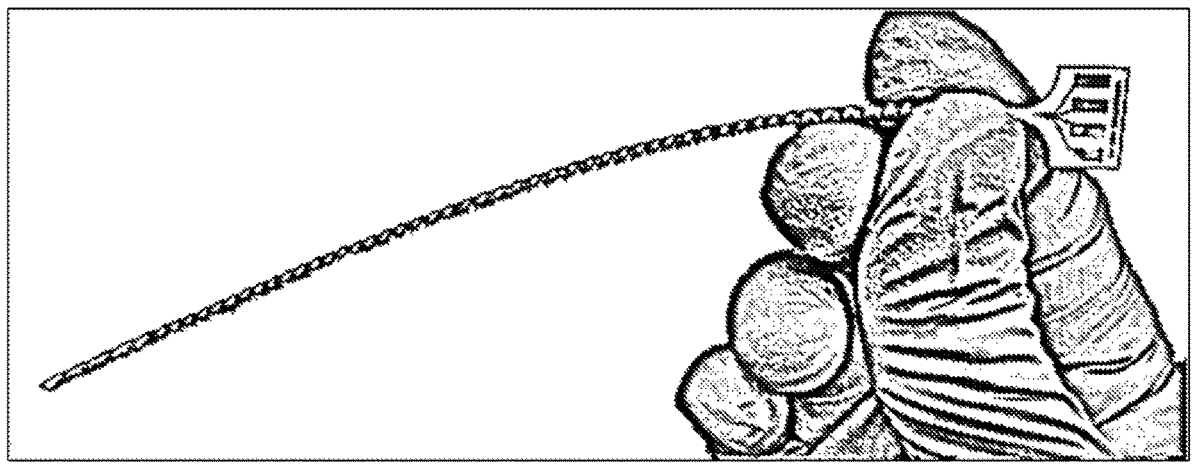
FIG. 4 shows an unspiraled lead assembly according to an embodiment of the invention.

FIG. 3 shows a spiraled lead assembly according to an embodiment of the invention. FIG. 4 shows an extended lead assembly according to an embodiment of the invention. The lead assembly can be monolithic, such that a single substrate (e.g., configured to different shapes) extends across the entire lead assembly. The lead assembly can include a cable having a proximal end 310 and a distal end 315. As used herein, the term "proximal end" refers to a first end of the main body, while the term "distal end" refers to a second end opposing the first end. For example, the proximal end may be an end of the main body, which is closest to the user, and the distal end may be an end of the main body, which is furthest from the user.

The cable may comprise a supporting structure and one or more conductive traces formed on a portion of supporting structure. As used herein, the term "formed on" refers to a structure or feature that is formed on a surface of another structure or feature, a structure or feature that is formed within another structure or feature, or a structure or feature that is formed both on and within another structure or feature. Further, the cable includes a set of electrodes 320 at (e.g., formed on, disposed at, attached to) distal end 315. Each electrode 320 and trace can include a conductive material.

At proximal end 310, each conductive trace can terminate at a conductive bonding pad 325. In some instances, the distal portion of the lead assembly (that includes electrodes 320) is rigid, while an intermediate portion that extends from the distal portion to the bonding pads (and includes the traces) is flexible. Bonding pads 325 can include a bonding material, which can be (for example) a conductive epoxy or a metallic solder or weld such as platinum. It will be appreciated that alternative connectors (e.g., to be used instead of in addition to bonding pads 325) are contemplated. For example, a mechanical connector (e.g., a pin and sleeve connector, snap and lock connector, flexible printed circuit connector) may be used.

In some embodiments, the supporting structure extends from proximal end 310 to the distal end 315. In some embodiments, the supporting structure may be made of one or more layers of dielectric material (i.e., an insulator). The dielectric material may be selected from the group of electrically nonconductive materials consisting of organic or inorganic polymers, ceramics, glass, glass-ceramics, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof. In other embodiments, the supporting structure may be made of one or more layers of dielectric material formed on a substrate. The substrate may be made from any type of metallic or non-metallic material.

The supporting structure can comprise one or more layers of dielectric material, and optionally the substrate, has a thickness (t) from proximal end 310 to distal end 315. In some embodiments, the thickness (t) is from 10 μm to 150 μm, for example about 50 μm or about 60 μm. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent. In some embodiments, the supporting structure 220 has a length (l) of 5 cm to 150 cm or 50 cm to 100 cm, e.g., about 75 cm (see, e.g., FIG. 2A). In some embodiments, the supporting structure has a width (w) from a first side to a second side. In some embodiments, the width (w) is from 25 μm to 5 mm, for example about 400 μm or about 1000 μm.

In some embodiments, the one or more conductive traces are a plurality of traces, for example, two or more conductive traces or from two to twenty-four conductive traces. The plurality of conductive trace are comprised of one or more layers of conductive material. The conductive material may include pure metals, metal alloys, combinations of metals and dielectrics, and the like. For example, the conductive material may be copper (Cu), gold (Au), silver (Ag), gold/chromium (Au/Cr), etc. In some embodiments, the conductive material also has thermal expansion characteristics or a coefficient of thermal expansion (CTE) that is approximately equal to that of CTE of the supporting structure. Matching the CTE of components that contact one another can be desirable because it eliminates the development of thermal stresses, which may occur during fabrication and the operation of the cable, and thus eliminates a known cause of mechanical failure in the components.

The one or more conductive traces may be deposited onto a surface of the supporting structure by using thin film deposition techniques well known to those skilled in the art such as by sputter deposition, chemical vapor deposition, metal organic chemical vapor deposition, electroplating, electroless plating, and the like. In some embodiments, the thickness of the one or more conductive traces is dependent on the particular impedance desired for conductor, in order to ensure excellent signal integrity (e.g., electrical signal integrity for stimulation or recording). For example, if a conductor having a relatively high impedance is desired, a small thickness of conductive material should be deposited onto the supporting structure. If, however, a signal plane having a relatively low impedance is desired, a greater thickness of electrically conductive material should be deposited onto the supporting structure. In certain embodiments, each of the one or more conductive traces has a thickness (d). In some embodiments, the thickness (d) is from 0.5 μm to 100 μm or from 25 μm to 50 μm, for example about 25 μm or about 40 μm. In some embodiments, each of the one or more conductive traces has a length (m) of about 5 cm to 200 cm or 50 cm to 150 cm, e.g., about 80 cm. In certain embodiments, each of the one or more conductive traces extends from proximal end 310 to distal end 315. In some embodiments, each of the one or more conductive traces has a width (y) from 2.0 µm to 500 µm, for example about 30 µm or about 50 µm.

As shown in FIG. 3, the lead assembly may be formed with a predetermined shape in accordance with aspects of the present disclosure. In particular, the lead assembly may be formed with a predetermined shape from a prefabricated wafer or panel of dielectric material or optionally a substrate. For example, the lead assembly may be laser cut from a prefabricated wafer or panel in a spiral shape. The spiral shape may include characteristics designed to maximize the length of the lead assembly that can be fabricated from a single wafer or panel. Conventionally, wafers or panels have a diameter, length, and/or width of less than 10 cm. In some embodiments, the characteristics of the spiral shape include a predetermined number of turns and a predetermined pitch (p) between each of the turns to maximize the overall length obtainable for the lead assembly. In certain embodiments, the spiral shape has 2 or more turns, for example from 2 to 25 turns, and a pitch (p) between each of the turns from 10 µm to 1 cm or from 250 µm to 2 mm, for example about 350 µm. Accordingly, the spiral shape can maximize the length of the lead assembly hat can be fabricated from a single wafer or panel. For example, a single wafer or panel with a limited diameter, length, and/or width of less than 10 cm, can be used to fabricate a lead assembly with a length of 5 cm to 150 cm, 10 cm to 100 cm, or 25 cm to 75 cm, e.g., about 15 cm, using the spiral shape.

The lead assembly may further comprise an electrode assembly at distal end 315. The electrode assembly can include the supporting structure and a set of microelectronic structures disposed on the supporting structure. The microelectronic structures can include electrodes 320, a wiring layer, and optional contact(s). In various embodiments, the supporting structure of the lead assembly and the supporting structure of the electrode assembly are the same structure (i.e., the supporting structure is continuous from the proximal end 310 to the distal end 315), which thus creates a monolithic cable. In some embodiments, the supporting structure for the electrode assembly comprising the one or more layers of dielectric material, and optionally the substrate, has a thickness (r) of from 10 µm to 150 µm, from 15 µm to 70 µm, from 30 µm to 60 µm, or from 40 µm to 60 µm. In some embodiments, the supporting structure has a width (v) that is from 25 µm to 10 mm, for example about 50 µm or about 5000 µm.

The wiring layer may be formed continuously of the one or more conductive traces and may be comprised of various metals or alloys thereof, for example, copper (Cu), gold (Au), silver (Ag), gold/chromium (Au/Cr), platinum (Pt), platinum/iridium (Pt/Ir), titanium (Ti), gold/titanium (Au/Ti), or any alloy thereof. The wiring layer may have a thickness (x) of from 0.5 µm to 100 µm, from 0.5 µm to 15 µm, from 0.5 µm to 10 µm, or from 0.5 µm to 5 µm. In some embodiments, a top surface of the wiring layer is coplanar with a top surface of the supporting structure. In other embodiments, the wiring layer is embedded within the supporting structure. In yet other embodiments, the wiring layer is formed on the top surface of the supporting structure and the top surface of the wiring layer is raised above the top surface of the supporting structure.

In some embodiments, each of the set of electrodes 320 is formed on the supporting structure and is in electrical contact with the wiring layer. Each electrode 320 may be comprised of conductive material such as copper (Cu), gold (Au), silver (Ag), gold/chromium (Au/Cr), platinum (Pt), platinum/iridium (Pt/Ir), titanium (Ti), gold/titanium (Au/Ti), or any alloy thereof, for example. Each electrode 320 may have a thickness (z) of from 0.1 µm to 50 µm, from 0.3 µm to 30 µm, from 0.5 µm to 20 µm, or from 1 µm to 15 µm. The set of electrodes 320 may be formed directly on the supporting structure or formed indirectly on the supporting structure. In some embodiments, a set of contacts are formed on the supporting structure and provide electrical contact between the set of electrodes 320 and the wiring layer. The contacts may be comprised of conductive material such as copper (Cu), gold (Au), silver (Ag), gold/chromium (Au/Cr), platinum (Pt), platinum/iridium (Pt/Ir), titanium (Ti), gold/titanium (Au/Ti), or any alloy thereof, for example.

Figure 5A:
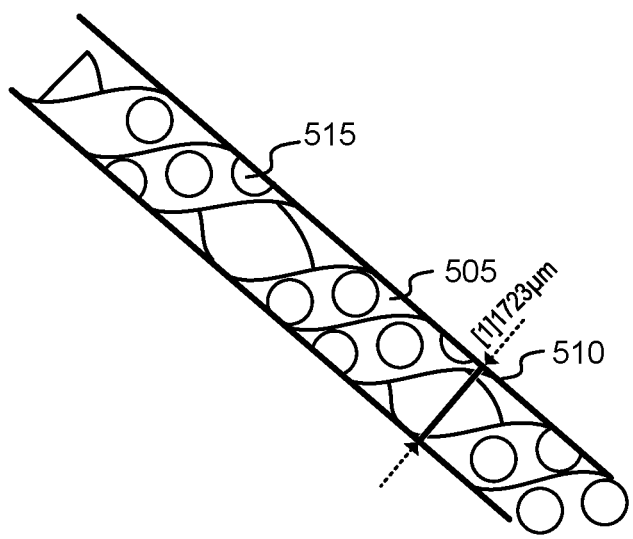
FIG. 5A shows electrodes arranged in a helical configuration and included within a deep brain stimulation system according to an embodiment of the invention.
Figure 5B:
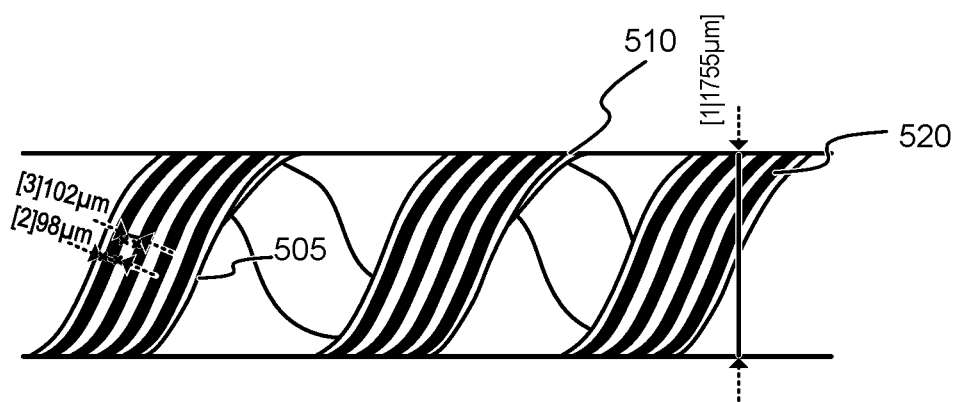
FIG. 5B shows leads arranged in a helical configuration and included within a deep brain stimulation system according to an embodiment of the invention.

FIG. 5A shows electrodes arranged in a helical configuration and included within a deep brain stimulation system according to an embodiment of the invention. FIG. 5B shows leads arranged in a helical configuration and included within a deep brain stimulation system according to an embodiment of the invention. As shown, a helical substrate 505 is configured in a helical shape around a supporting structure 510. A set of electrodes 515 and a set of traces 520 can be formed on helical substrate 505. Substrate 505 is wrapped such that it forms a helical shape. As used herein, the phrases "helical" refer to a device fabricated with plural helixes or helices, which are a type of smooth space curve, i.e. a curve in three-dimensional space. The helix may be wound clockwise direction or anti-clockwise direction. The helix have the property that a tangent line at any point makes a constant angle with a fixed line called the axis. It will be appreciated that the collective set of electrodes 515 and the set of traces 520 (and/or each individual trace 520) can also be helically shaped.

Substrate 505 may extend along and/or may be helically positioned along a portion of the lead assembly. The portion can include substantially the entire length of the one or more conductive traces and/or of the set of electrodes. Alternatively, the helical portion may be the portion of the cable extending between the proximal end and the distal end but not including the a connecting portion (e.g., that includes bonding pads and/or one or more other connectors). In certain embodiments, the helical portion of the cable comprises one or more characteristics including a radius, a helix angle, a pitch (rise of the helix for one turn), a helix length, and/or a total rise of the helix. The radius may be from 200 µm to 900 µm, from 250 µm to 700 µm, or from 400 µm to 650 µm, for example, about 580 µm. The helix angle may be from 10° to 85°, from 40° to 65°, or from 42° to 60°, for example, about 55°. A pitch may be from 100 µm to 2 mm, from 200 µm to 400 µm, or from 600 µm to 1600 µm, for example, about 720 µm. The helix length may be from 5 cm to 150 cm or 50 cm to 100 cm, e.g., about 75 cm, from the proximal end to the distal end. The total rise may be from 5 cm to 125 cm or 25 cm to 75 cm, e.g., about 50 cm, from the proximal end to the distal end.

In some instances, a characteristic of the helix at a first portion of the lead assembly that includes electrodes 515 is different than a characteristic of the helix at a second portion of the lead assembly that includes traces 520. In some embodiments, the first portion (that supports electrodes 515) has a first helical structure. The first portion may be defined as the last 1 cm to 15 cm of the cable on the distal end of the cable. In certain embodiments, the first portion comprises tight helixes (e.g., for tissue penetration as with deep brain stimulation or connection to a device such as a neurostimulator) with characteristics including a radius from 200 µm to 900 µm, a helix angle from 10° to 85°, and a pitch from 200 µm to 400 µm. In some embodiments, the second portion (that supports traces 520) has a second helical structure. In certain embodiments, the second portion comprises loose helixes with characteristics including a radius from 200 µm to 900 µm, a helix angle from 10° to 85°, and a pitch from 600 µm to 1600 µm.

In some instances, part or all of the lead assembly further includes a housing that is disposed on, positioned on and/or encases the electrodes and/or leads. The housing may be comprised of a medical grade polymer material. In some embodiments, the medical grade polymer is thermosetting or thermoplastic. For example, the medical grade polymer may be a soft polymer such as silicone, a polymer dispersion such as latex, a chemical vapor deposited poly(p-xylylene) polymer such as parylene, or a polyurethane such as Bionate® Thermoplastic Polycarbonate-urethane (PCU) or CarboSil® Thermoplastic Silicone-Polycarbonate-urethan (TSPCU).

Figure 5C:
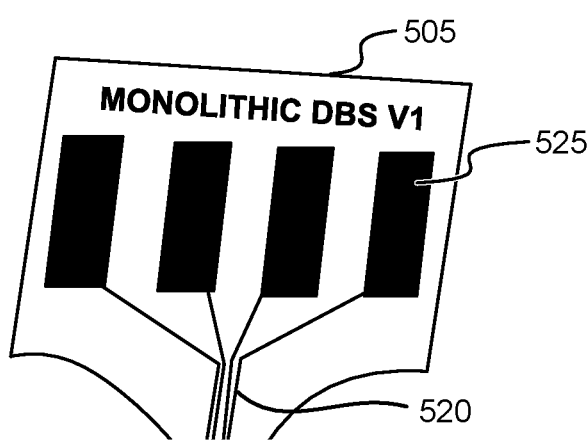
FIG. 5C shows bonding pads included within a deep brain stimulation system according to an embodiment of the invention.

At a proximal end of the lead assembly, substrate 505 can flatten such that it is no longer in a helical shape, as shown in FIG. 5C. Further, in some instances, supporting structure 510 is absent at the proximal end or also is in a flat (non-cylindrical) shape. Each trace 520 can terminate at a bonding pad 525. In some instances, bonding pads 525 and traces 520 include a same material and/or same composition. The lead assembly may be configured such that there is, for example, a 1:1 ratio between traces and bonding pads, or multiple traces 520 may connect to an individual bonding pad 525.

FIGS. 6A-6F show stages of manufacture of a lead assembly (e.g., used to manufacture the lead assembly depicted in FIGS. 4 and 5A-5C) according to an embodiment of the invention. More specifically, FIGS. 6A-6F illustrate stages during a process for forming a helically shaped substrate, which can support electrical traces and/or electrodes.

Figure 6A:
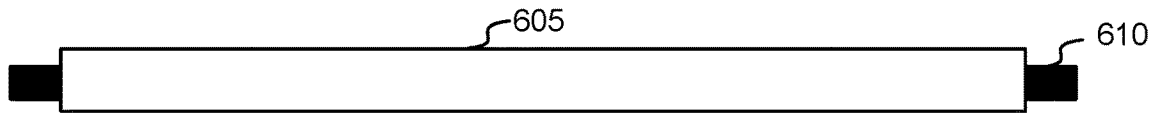
FIGS. 6A-6F show stages of manufacture of a lead assembly according to an embodiment of the invention.

As shown in FIG. 6A, a coating 605 can be formed on a mandrel 610. Coating 605 can include a material that can facilitate withdrawal of mandrel 610 towards the end of the process. For example, coating 605 can include a heat shrink tube, a fluoro polymer, polytetrafluoroethylene and/or Teflon, and the heat shrink tube can be recovered at (for example) 195° C. Mandrel 610 can include a rigid material, metal material, and/or fluoro polymer (e.g., polytetrafluoroethylene).

Figure 6B:

As shown in FIG. 6B, the mandrel 610 can be inserted into a thermoplastic tubing 615 (e.g., comprising thermoplastic polyurethane). Thermoplastic tubing 615 can include a reflowable material and/or can include (for example) CarboSil tube).

Figure 6C:
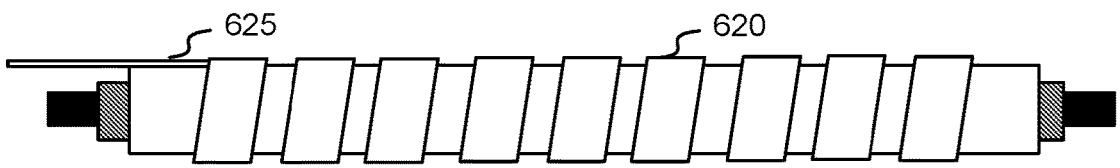

A substrate 620 can then be wrapped around thermoplastic tubing 615. (FIG. 6C.) A first portions 620 of substrate can be wrapped to include (for example) regularly spacing between subsequent wraps across the entire mandrel or across each of one or more portions of the mandrel. The substrate can include a thin-film material and/or polymer, such as liquid-crystal polymer (LCP). The wrapped mandrel can then be thermoformed to define the helical shape. While first portion 620 of the substrate can be wrapped in a helical portion, a second portion 625 can remain planar to support a connector (e.g., a bond pad). First portion 620 and second portion 625 of the substrate can, but need not, have a same composition and/or thickness.

Figure 6D:
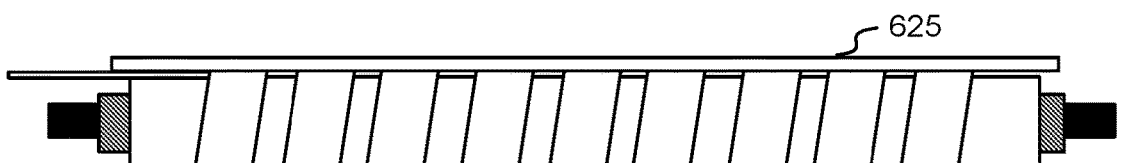

The wrapped mandrel can then be inserted into a peelable heat-shrink tube (and/or tube including a fluoro polymer) 630. The assembly can then be recovered (e.g., at 195° C.) to shrink the heat-shrink tube. (FIG. 6D.) The shrunk heat-shrink tube 630 can apply pressure to the wrapped mandrel to hold the assembly together. During the heating process, thermoplastic tubing 615 can further reflow, which can glue into first portion 620 of substrate. The reflow can cause the assembly to have a smoother surface, such that first portion 620 of the substrate is not raised relative to thermoplastic tubing 615.

Figure 6E:
Figure 6F:
Figure 7:
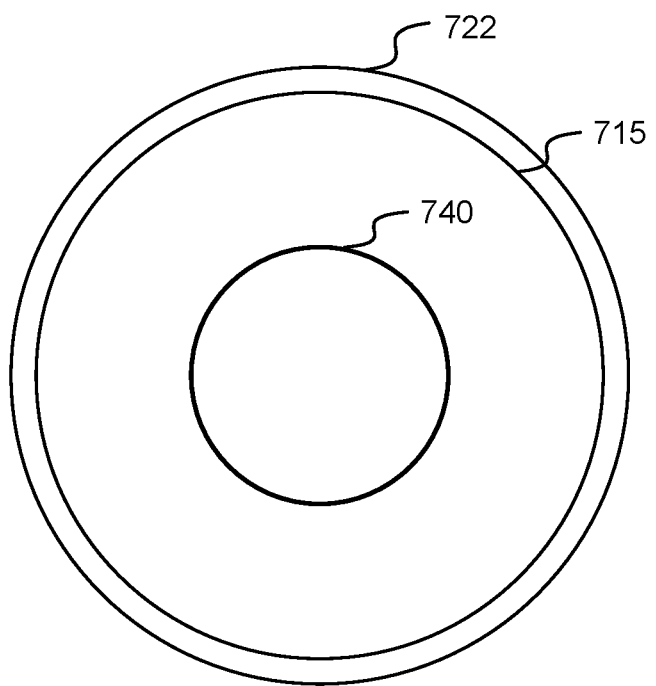
FIG. 7 shows cross-section perspective of a lead assembly according to an embodiment of the invention.

The assembly can then be cooled (e.g. to room temperature), and heat-shrink tube 630 can be peeled away. (FIG. 6E.) Mandrel 610 and coating 605 can then be removed (FIG. 6F). As shown in the cross-section illustrated in FIG. 7, a resulting lead assembly the includes a stylet lumen 740 through a middle portion of the lead assembly. The lead assembly can include a helically wrapped substrate 722 and a thermoplastic tubing 615 or other supporting structure. The depicted cross section shows substrate 722 as extending fully around thermoplastic tubing 615. However, it will be appreciated that—due to the helical nature of the substrate, it may extend across only a portion of the circumference for any given cross-section corresponding to a specific position along the lead assembly's length. A diameter of lumen 740 may be (for example) at least 10%, at least 25%, at least 33% or at least 50% of a diameter of the helically wrapped portion of the lead assembly. A diameter of lumen 740 may be (for example) less than 90%, less than 75%, less than 66% or less than 50% of a diameter of the helically wrapped portion of the lead assembly.

During an implantation process, a stylet (e.g., a rigid thin object, such as a metallic thin object) can be inserted into stylet lumen 740. The stylet can provide rigidity to the lead assembly to facilitate implanting the device to a target position.

Thus, FIGS. 6A-6F illustrate how a thermoplastic can be used to manufacture a lead assembly that includes a central lumen. In the illustrated example, a thermoplastic tubing is reflowed to essentially glue the helical substrate and an underlying material together, such that a supporting mandrel can be removed. Another approach for manufacturing a lead assembly with a central lumen is to use a thermoset material.

FIGS. 8A-8F show stages of manufacture of a lead assembly using a thermoset material according to an embodiment of the invention. More specifically, FIGS. 8A-8F illustrate stages during a formation of a helically shaped substrate, which can support electrical traces and/or electrodes.

Figure 8A:
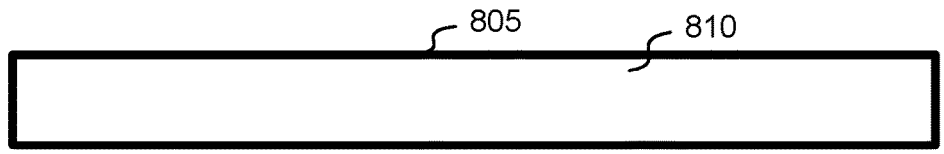
FIGS. 8A-8F show stages of manufacture of a lead assembly according to an embodiment of the invention.

As shown in FIG. 8A, a coating 805 can be applied to a tubing 810. Tubing 810 can include (for example) a thermoset material and/or silicone tubing. Coating 805 can include (for example) diluted liquid silicone resin. In some instances, coating 805 is applied after the surface of tubing 810 is prepared for adhesion (e.g., by performing a plasma activation or oxygen plasma activation). After coating 805 is applied, the coated tubing can be partially thermally cured (e.g., to a 50-100 µm thickness). This partial curing can result in a surface of the tubing being tacky.

Figure 8B:

A mandrel 815 can be inserted into the coated tubing. (FIG. 8B.) Mandrel 815 can include and/or can be (for example) a rigid material, metal material, and/or fluoro polymer (e.g., polytetrafluoroethylene). Mandrel 815 can include be coated, such as with a fluoro polymer, polytetrafluoroethylene and/or Teflon rigid material, metal material, and/or fluoro polymer (e.g., polytetrafluoroethylene).

Figure 8C:

A first portion 820 of a substrate can then be wrapped around the coated tubing 810. (FIG. 8C.) In some instances, prior to the wrapping, a surface of first portion 820 of the substrate can be prepared for adhesion by (for example) performing a plasma activation (e.g., oxygen plasma activation).

First portions 820 of the substrate can be wrapped to include (for example) regularly spacing between subsequent wraps across the entire mandrel or across each of one or more portions of the mandrel. The substrate can include a thin-film material and/or polymer, such as liquid-crystal polymer (LCP). While first portion 820 of the substrate can be wrapped in a helical portion, a second portion 825 can remain planar to support a connector (e.g., a bond pad). First portion 820 and second portion 825 of the substrate can, but need not, have a same composition and/or thickness.

Figure 8D:
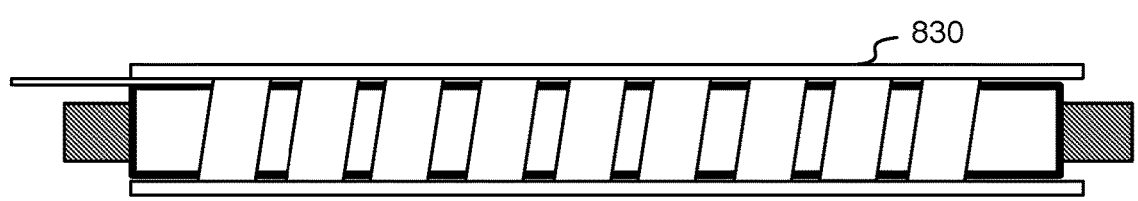

The wrapped mandrel can then be inserted into a peelable heat-shrink tube (and/or tube including a fluoro polymer and/or PEELZ) 830. The assembly can then be recovered (e.g., at 195° C.) to shrink the heat-shrink tube. (FIG. 8D.) The shrunk heat-shrink tube 830 can apply pressure to the wrapped mandrel to hold the assembly together. The partially cured coating 805 on tubing 810 can adhere to the wrapped first portion 820 of the substrate due to covalent bonding under heat and pressure, which can fully cure coating 805.

Figure 8E:
Figure 8F:
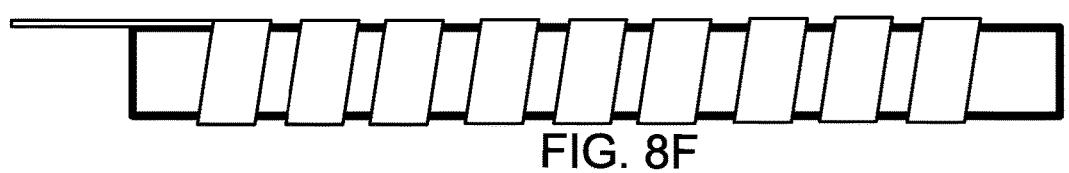

The assembly can then be cooled (e.g. to room temperature), and heat-shrink tube 830 can be peeled away. (FIG. 8E.) Mandrel 815 can then be removed (FIG. 8F).

Figure 9:
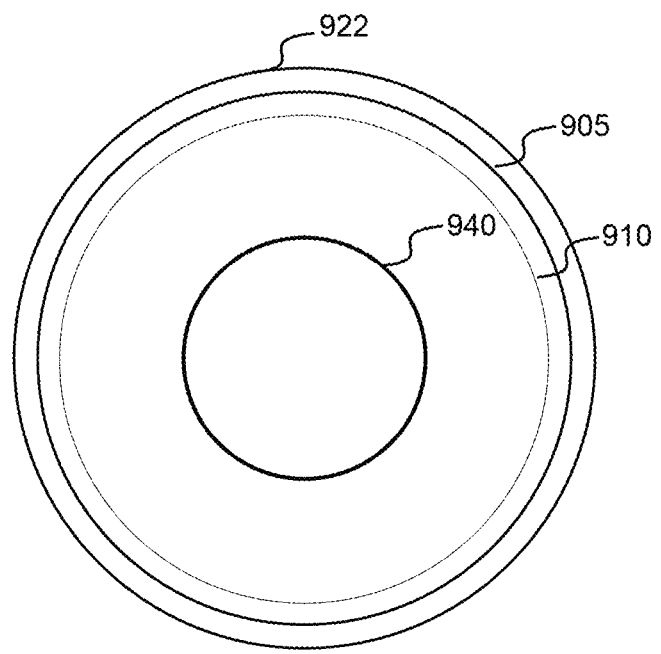
FIG. 9 shows a cross-section perspective of a lead assembly according to an embodiment of the invention.

As shown in the cross-section illustrated in FIG. 9, a resulting lead assembly the includes a stylet lumen 940 through a middle portion of the lead assembly. The lead assembly can include a helically wrapped substrate 922 and a tubing 910 that is coated with a coating 905 (e.g., a thermoset coating), which can facilitate adhering substrate 922 to tubing 910. The depicted cross section shows substrate 922 as extending fully around tubing 910. However, it will be appreciated that—due to the helical nature of the substrate, it may extend across only a portion of the circumference for any given cross-section corresponding to a specific position along the lead assembly's length. A diameter of lumen 940 may be (for example) at least 10%, at least 25%, at least 33% or at least 50% of a diameter of the helically wrapped portion of the lead assembly. A diameter of lumen 940 may be (for example) less than 90%, less than 75%, less than 66% or less than 50% of a diameter of the helically wrapped portion of the lead assembly.

FIGS. 10A-10E show various views of a lead assembly according to an embodiment of the invention. The depicted lead assembly includes one manufactured in accordance with the manufacture illustrated in FIGS. 8A-8F. The lead assembly again includes a proximal section 1005 that includes multiple bonding pads. The lead assembly further includes a distal section. The distal section includes a first distal-section portion 1010 (shown in FIG. 10D) and a second distal-section portion 1015 (shown in FIG. 10C), and a middle section that extends between proximal section 1005 and the distal section and includes a middle-section portion 1020 (shown in FIG. 10E).

Across the distal section and middle section, a substrate 1025 is wrapped in a helically shape. At proximal section 1005, substrate 1025 is in a planar configuration. At the distal section, a set of electrodes 1030 is disposed on the helically shaped substrate 1025. A lumen 1035 extends through the part of the lead assembly that includes the wrapped substrate 1025. Each electrode 1030 can be connected to an electrical trace 1040 that extends from the electrode to a bonding pad—in a helical shape—along the middle section (along substrate 1025).

FIGS. 11A-11F show stages of manufacture of a lead assembly using a thermoset material according to an embodiment of the invention. More specifically, FIGS. 11A-11F illustrate stages during a formation of a helically shaped substrate, which can support electrical traces and/or electrodes.

Figure 11A:
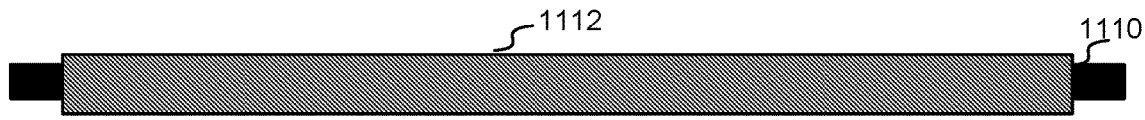
FIGS. 11A-11F show stages of manufacture of a lead assembly according to an embodiment of the invention.

As shown in FIG. 11A, a mandrel 1110 can be inserted into a silicone tubing 1112. (It will be appreciated that, alternatively, a coating can be applied to mandrel 1110). Mandrel 1110 can include can include and/or can be (for example) a rigid material, metal material, and/or fluoro polymer (e.g., polytetrafluoroethylene). Mandrel 1110 can include be coated, such as with a fluoro polymer, polytetrafluoroethylene and/or Teflon rigid material, metal material, and/or fluoro polymer (e.g., polytetrafluoroethylene). Silicone tubing 1112 can have an inner diameter that is (for example) less than 0.050, less than 0.030, less than 0.020 and/or approximately 0.020 inches. Silicone tubing 1112 can have an outer diameter that is (for example) less than 0.100, less than 0.050, less than 0.040 and/or approximately 0.037 inches. Mandrel 1110 can have an outer diameter than is (for example) greater than 0.005, greater than 0.010, approximately 0.018, less than 0.020, and/or less than 0.030 inches.

Figure 11B:

As shown in FIG. 11B, the tubing-mandrel assembly can be inserted into a thermoplastic tubing 1115 (e.g., comprising thermoplastic polyurethane). Thermoplastic tubing 1115 can include a reflowable material and/or can include (for example) CarboSil tube. Thermoplastic tubing 1115 can have an inner diameter that is (for example) less than 0.10, less than 0.080, less than 0.050, approximately 0.042, greater than 0.030 and/or greater than 0.040 inches. Thermoplastic tubing 1115 can have an outer diameter that is (for example) less than 0.100, less than 0.050, approximately 0.046, greater than 0.030, and/or greater than 0.040 inches.

Figure 11C:
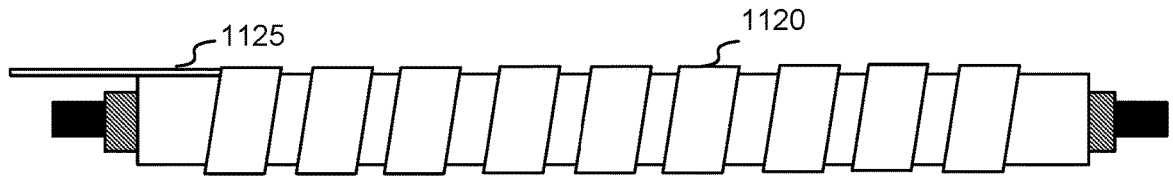

A first portion 1120 of a substrate can then be wrapped around thermoplastic tubing 1115. (FIG. 11C.) The wrapping can be performed to produce (for example) regularly spacing between subsequent wraps across the entire thermoplastic tubing or across each of one or more portions of the thermoplastic tubing. The substrate can include a thin-film material and/or polymer, such as liquid-crystal polymer (LCP). The wrapped structure can then be thermoformed (e.g., at 150° C.) to define the helical shape. While first portion 1120 of the substrate can be wrapped in a helical portion, a second portion 1125 can remain planar to support a connector (e.g., a bond pad). First portion 1120 and second portion 1125 of the substrate can, but need not, have a same composition and/or thickness.

Figure 11D:
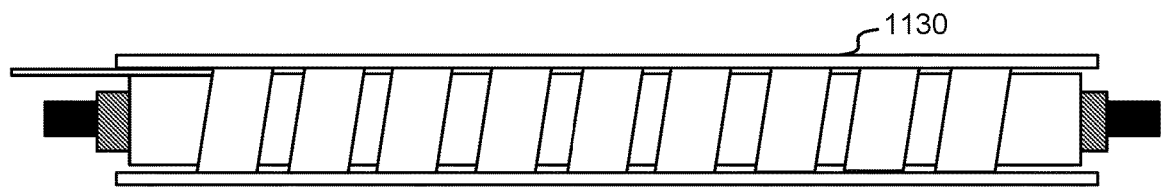

The wrapped structure can then be inserted into a peelable heat-shrink tube (and/or tube including a fluoro polymer and/or PEELZ) 1130. The assembly can then be recovered (e.g., at 195° C.) to shrink the heat-shrink tube. (FIG. 11D.) The shrunk heat-shrink tube 630 can apply pressure to the wrapped mandrel to hold the assembly together. During the heating process, thermoplastic tubing 1115 can further reflow, which can glue into first portion 1120 of substrate. The reflow can cause the assembly to have a smoother surface, such that first portion 1120 of the substrate is not raised relative to thermoplastic tubing 1115.

Figure 11E:
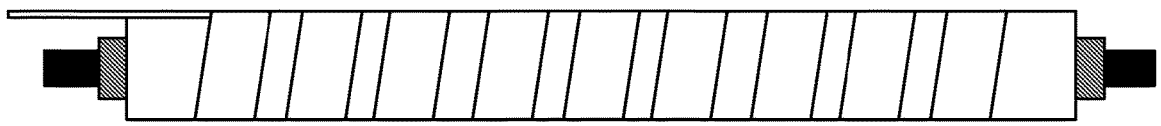
Figure 11F:
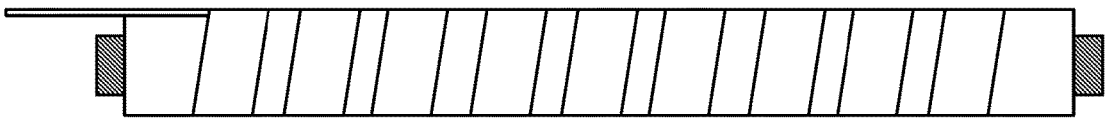

The assembly can then be cooled (e.g. to room temperature), and heat-shrink tube 1130 can be peeled away. (FIG. 11E.) Mandrel 1115 can then be removed (FIG. 11F). Thus, both thermosetting and thermoforming (e.g., using heat-shrink tube 1130 and thermoplastic tubing 1115, respectively) can stabilize the helical position of first portion 1120 of the substrate.

Figure 12:
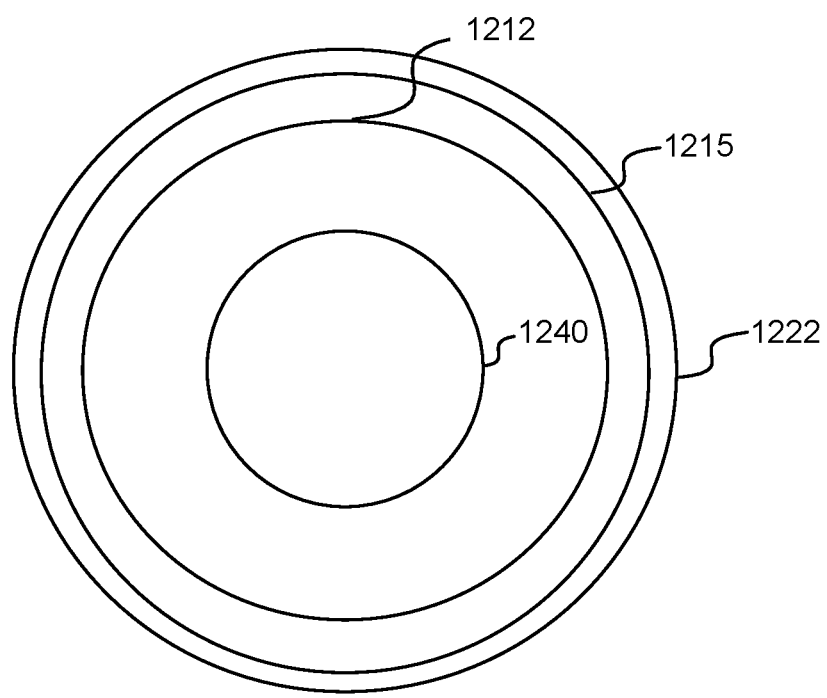
FIG. 12 shows a cross-section perspective of a lead assembly according to an embodiment of the invention.

As shown in the cross-section illustrated in FIG. 12, a resulting lead assembly the includes a stylet lumen 1240 through a middle portion of the lead assembly. The lead assembly can include a helically wrapped substrate 1222, which is wrapped around thermoplastic tubing 1215, which is adhered to silicone tubing 1212. The depicted cross section shows substrate 1222 as extending fully around thermoplastic tubing 1215. However, it will be appreciated that—due to the helical nature of the substrate, it may extend across only a portion of the circumference for any given cross-section corresponding to a specific position along the lead assembly's length. A diameter of lumen 1240 may be (for example) at least 10%, at least 25%, at least 33% or at least 50% of a diameter of the helically wrapped portion of the lead assembly. A diameter of lumen 1240 may be (for example) less than 90%, less than 75%, less than 66% or less than 50% of a diameter of the helically wrapped portion of the lead assembly.

Various designs and processes disclosed herein can facilitate generation of a stimulation system that has a small outer diameter, which can reduce inflammation and damage while implanting the system or while it is positioned at an implant location. In some instances, the stimulation system (e.g., and/or a lead body) can have an outer diameter that is less than 20 mm, less than 10 mm, less than 5 mm, less than 2 mm, less than 1.5 mm, less than 1.4 mm, and/or approximately 1.2 mm. In some instances, the stimulation system can be designed to include a large number of electrodes and traces (e.g., approximately 8, 16, 32 or 64 electrodes and/or more than 4, more than 8, more than 16 or more than 32 electrodes) while still having a small outer diameter (e.g., that is less than 20 mm, less than 10 mm, less than 5 mm, less than 2 mm, less than 1.5 mm, less than 1.4 mm, and/or approximately 1.2 mm).

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

It is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure.

While the principles of the disclosure have been described above in connection with specific apparatuses and methods, it is to be clearly understood that this description is made only by way of example and not as limitation on the scope of the disclosure.

What is claimed is:

1. A stimulation system comprising:
   one or more stimulating components, wherein each of the one or more stimulating components includes:
      one or more electrodes; and
      one or more leads, wherein each lead of the one or more leads is connected at a first end of the lead to an electrode of the one or more electrodes and is connected at a second end of the lead to a bonding pad of one or more first bonding pads,
   a cylindrical substrate, wherein the cylindrical substrate forms a hollow cylinder, and wherein each of the one or more stimulating components is secured to an outer surface of the cylindrical substrate along a length of the one or more leads; and
   a skull-mount package that includes:
      electronics that identify stimulation parameters; and
      one or more second bonding pads, wherein a bonding pad of the one or more first bonding pads of each lead of the one or more leads is directly electrically and physically connected to a second bonding pad of the one or more second bonding pads.

2. The stimulation system of claim 1, wherein each of the one or more stimulating components further includes an insulating substrate, and wherein each of the one or more electrodes is disposed on the insulating substrate.

3. The stimulation system of claim 1, wherein each of the one or more stimulating components is wrapped around to an outer surface of the cylindrical substrate.

4. The stimulation system of claim 1, wherein the cylindrical substrate comprises a thermoplastic or thermoset material.

5. The stimulation system of claim 1, further comprising:
   a fluoropolymer coating that at least partially surrounds the secured one or more stimulating components.

6. The stimulation system of claim 1, wherein the one or more stimulating components includes a plurality of stimulating components, and wherein the plurality of stimulating components are secured to the surface of the cylindrical substrate such that the one or more stimulating components do not overlap with each other.

7. The stimulation system of claim 1, wherein:
   the one or more electrodes includes at least 32 electrodes; and
   a diameter of the stimulation system across a length-wise portion that includes at least one of the one or more stimulating components is less than 10 mm.

8. The stimulation system of claim 1, wherein:
   the one or more electrodes includes less than 9 electrodes; and
   a diameter of the stimulation system across a length-wise portion that includes at least one of the one or more stimulating components is less than 2 mm.

9. The stimulation system of claim 1, wherein the one or more stimulating components includes a first set of stimulating components and a second set of stimulating components, wherein spacing between and/or sizes of electrodes within the first set of stimulating components differ from spacing between and/or sizes of electrodes within the second set of stimulating components.

10. A method of manufacturing a lead assembly comprising:
   disposing a set of electrodes and a set of electrical traces on a substrate, wherein each of the set of electrodes is connected to an electrical trace of the set of electrical traces;
   inserting a mandrel through a tubing;
   wrapping the substrate around the tubing such that the substrate is in a helical shape;
   heating the substrate-wrapped tubing and mandrel prior to inserting the substrate-wrapped tubing and mandrel into a heat-shrink tube;

inserting the substrate-wrapped tubing and mandrel into the heat-shrink tube;
heating, subsequent to the insertion, the heat-shrink tube;
removing the heat-shrink tube from the substrate-wrapped tubing; and
removing the mandrel from the substrate-wrapped tubing.

11. The method of claim 10, wherein the tubing includes a thermoset material.

12. The method of claim 10, wherein the tubing includes a thermoplastic material.

13. The method of claim 10, wherein the mandrel includes a metal mandrel coated with a fluoro-polymer.

14. The method of claim 10, wherein the substrate includes a thin-film material.

15. The method of claim 10, wherein a first portion of the substrate is wrapped around the tubing and a second portion of the substrate remains unwrapped.

16. The method of claim 15, further comprising disposing a set of bonding pads on the second portion, wherein each trace of the set of electrical traces connects to a bonding pad of the set of bonding pads.

17. A method of implanting an implantable device, the method comprising:
implanting a lead assembly into a brain of a person, wherein the lead assembly includes:
  stimulating components including:
    one or more electrodes;
    one or more leads, wherein each lead of the one or more leads is connected at a first end of the lead to an electrode of the one or more electrodes and is connected at a second end of the lead to a bonding pad of the one or more bonding pads; and
  a cylindrical substrate, wherein the cylindrical substrate forms a hollow cylinder, and wherein each lead of the one or more stimulating components is secured to an outer surface of the cylindrical substrate along a length of the lead;
mounting a neurostimulator to a skull of the person; and
bonding the lead assembly with the neurostimulator.

18. The method of claim 17, wherein:
a lumen extends through a supporting structure;
implanting the lead assembly includes:
  inserting a rigid stylus through the lumen;
  moving a distal end of the lead assembly to a target location while the rigid stylus is inserted through the lumen; and
  removing the rigid stylus from the lumen.

* * * * *